United States Patent
Erickson et al.

(10) Patent No.: US 6,809,807 B1
(45) Date of Patent: Oct. 26, 2004

(54) BODY FLUID ANALYTE MEASUREMENT

(75) Inventors: Brian J. Erickson, Woodbury, MN (US); Philip J. Stout, Roseville, MN (US); Joel R. Racchini, Edina, MN (US)

(73) Assignee: Integ, Inc., St. Paul, MN (US)

( * ) Notice: Subject to any disclaimer, the term of this patent is extended or adjusted under 35 U.S.C. 154(b) by 0 days.

(21) Appl. No.: 09/264,786

(22) Filed: Mar. 9, 1999

(51) Int. Cl.[7] .................................................. G01J 1/00
(52) U.S. Cl. ....................................................... 356/213
(58) Field of Search ............................... 356/213–236, 356/36–50, 51; 250/343, 344, 345, 341.1, 339.11

(56) References Cited

U.S. PATENT DOCUMENTS

| | | |
|---|---|---|
| 4,157,470 A | 6/1979 | Kotaka et al. |
| 4,266,131 A | 5/1981 | Ahjopalo et al. |
| 4,288,693 A | 9/1981 | Fabinski et al. |
| 4,320,297 A | 3/1982 | Cederstrand et al. |
| 4,370,553 A | 1/1983 | Waycaster et al. |
| 4,394,575 A | 7/1983 | Nelson |
| 4,468,561 A | 8/1984 | Speeter |
| 4,501,968 A | 2/1985 | Ebi et al. |
| 4,520,265 A | 5/1985 | Griggs et al. |
| 4,663,530 A | 5/1987 | Shields |
| 4,855,601 A | 8/1989 | Savoyet |
| 4,950,900 A | 8/1990 | Takeuchi et al. |
| 4,975,581 A | 12/1990 | Robinson et al. |
| 5,258,620 A | 11/1993 | Sueyasu et al. |
| 5,582,184 A | 12/1996 | Erickson et al. |
| 5,682,233 A | 10/1997 | Brinda |
| 5,786,226 A | 7/1998 | Böcker et al. |
| 5,823,973 A | 10/1998 | Racchini et al. |
| 6,028,311 A | * 2/2000 | Sodickson et al. ........ 250/343 |

OTHER PUBLICATIONS

Wilks, "Filter Analyzers v. Process FT–IR Spectrometers, Continued", 10(9) Spectroscopy 23, Nov./Dec. 1995, 1 page.

* cited by examiner

*Primary Examiner*—Tu T. Nguyen
(74) *Attorney, Agent, or Firm*—Carol M. LaSalle; Bozicevic, Field & Francis, LLP

(57) ABSTRACT

An analyte (e.g., glucose) is tested in a sample (e.g., blood or blood-free interstitial fluid) having both the analyte and other constituents (e.g., protein). The analyte has an absorption peak over a narrow bandwidth at a characteristic wavelength. The other constituents have an absorption over a broad bandwidth. The broad bandwidth includes and is broader than the narrow bandwidth. Radiant energy (e.g., IR radiation) is directed at the sample. The energy has a source bandwidth including the broad bandwidth. The sample absorbs a portion of the energy. A remainder of the energy is available for analysis. The remainder is analyzed by filtering the remainder into an analyte portion and a reference portion. The analyte portion contains substantially only the narrow bandwidth. The reference portion contains substantially only the broad bandwidth. The analyte portion and the reference portion are measured and compared to calculate an amount of the analyte in the sample.

13 Claims, 7 Drawing Sheets

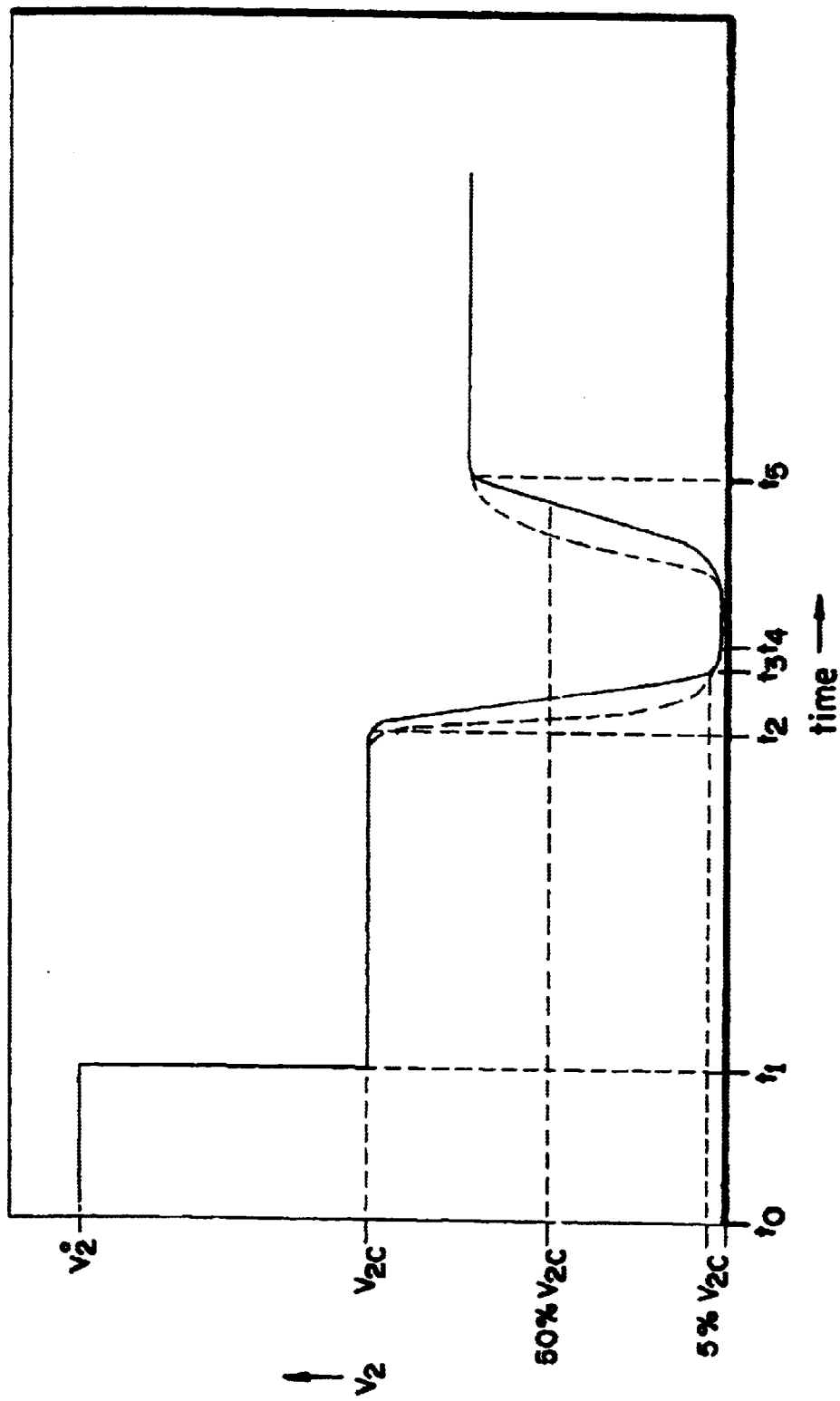

BODY FLUID ANALYTE MEASUREMENT

TECHNICAL FIELD

This invention pertains to a method and apparatus for testing analytes of a body fluid. More particularly, this invention pertains to such testing using absorption of light (visible or not visible) to test for the analytes.

BACKGROUND

Commonly assigned U.S. Pat. Nos. 5,682,233; 5,582,184; and 5,823,973 teach methods and apparatuses for testing for body fluid constituents. For example, these patents teach method and apparatus for determining a level of blood glucose in a minimally invasive manner by testing for glucose in interstitial fluid. More specifically, these patents teach a method for drawing a sample of substantially blood-free interstitial fluid and subsequently testing the sample for constituents. The testing may be done in any one of a number of ways (e.g., colormetric or electro-chemical testing). A preferred testing method is identified as infrared (IR) absorption testing.

In IR absorption testing, an IR source directs a band of IR wavelengths to a collected sample. Certain wavelengths (e.g., 1040 cm$^{-1}$) are absorbed by glucose. The amount of such absorption provides an indication of the amount of glucose in the sample. In turn, this information permits calculating the patient's blood glucose level.

In addition to containing IR absorbing glucose (or other desired constituent to be tested), the sample may contain other elements that absorb IR in the same spectral range that glucose absorbs IR energy. For example, protein and blood cells absorb IR in such a spectral range. In fact, these components absorb a greater portion of the IR radiation than the glucose to be measured. IR absorption by these components complicates attempts to measure the glucose in a sample. Providing techniques to draw a substantially blood free sample (or otherwise filtering blood cells out of the sample) relieves the complexity. However, remaining components (e.g., protein) continue to have a substantial influence on the amount of IR being absorbed by the sample. Further, water in the sample absorbs a very high portion of the IR energy.

Therefore, there is a need for an apparatus and method that detects and measures a body fluid analyte by spectral testing in a sample containing other constituents that absorb light wavelengths (visible or invisible) in the same spectral range in which the desired body fluid analyte absorbs light wavelengths.

SUMMARY

According to a preferred embodiment of the present invention, a method and apparatus are disclosed for testing for an analyte in a sample having both the analyte and other constituents. The analyte has an absorption peak over a narrow bandwidth at a characteristic wavelength. The other constituents have an absorption of a broad bandwidth. The broad bandwidth includes and is broader than the narrow bandwidth. Radiant energy is directed at the sample from a source having a source bandwidth including the broad bandwidth. The sample absorbs a portion of the energy. A remainder of the energy is available for analysis. The remainder is analyzed by filtering the remainder into a test portion and a reference portion. The test portion contains substantially only the narrow bandwidth. The reference portion contains substantially only the broad bandwidth. The test portion and the reference portion are measured and compared to calculate an amount of the analyte in the sample.

BRIEF DESCRIPTION OF THE DRAWINGS

FIG. 5 is a graph illustrating a voltage output of a reference IR detector of the apparatus of FIG. 3 versus time during a sampling and measuring process according to the flow chart of FIG. 4.

DETAILED DESCRIPTION

Referring now to the several drawing figures in which identical elements are numbered identically throughout, a description of the preferred embodiment of the present invention will now be provided.

Throughout this description, the present invention will be described with reference to testing for glucose in a sample of interstitial fluid collected and deposited on an absorbent membrane as taught in U.S. Pat. Nos. 5,682,233; 5,582,184; and 5,823,973, the teachings and description of which are incorporated herein by reference as though set forth in full. While such a use illustrates a preferred embodiment of the present invention, it is intended the present invention is applicable to testing for a wide variety of constitutes in blood-free as well as blood-containing body fluids and is applicable to a wide range of testing wavelengths.

Figure 1:
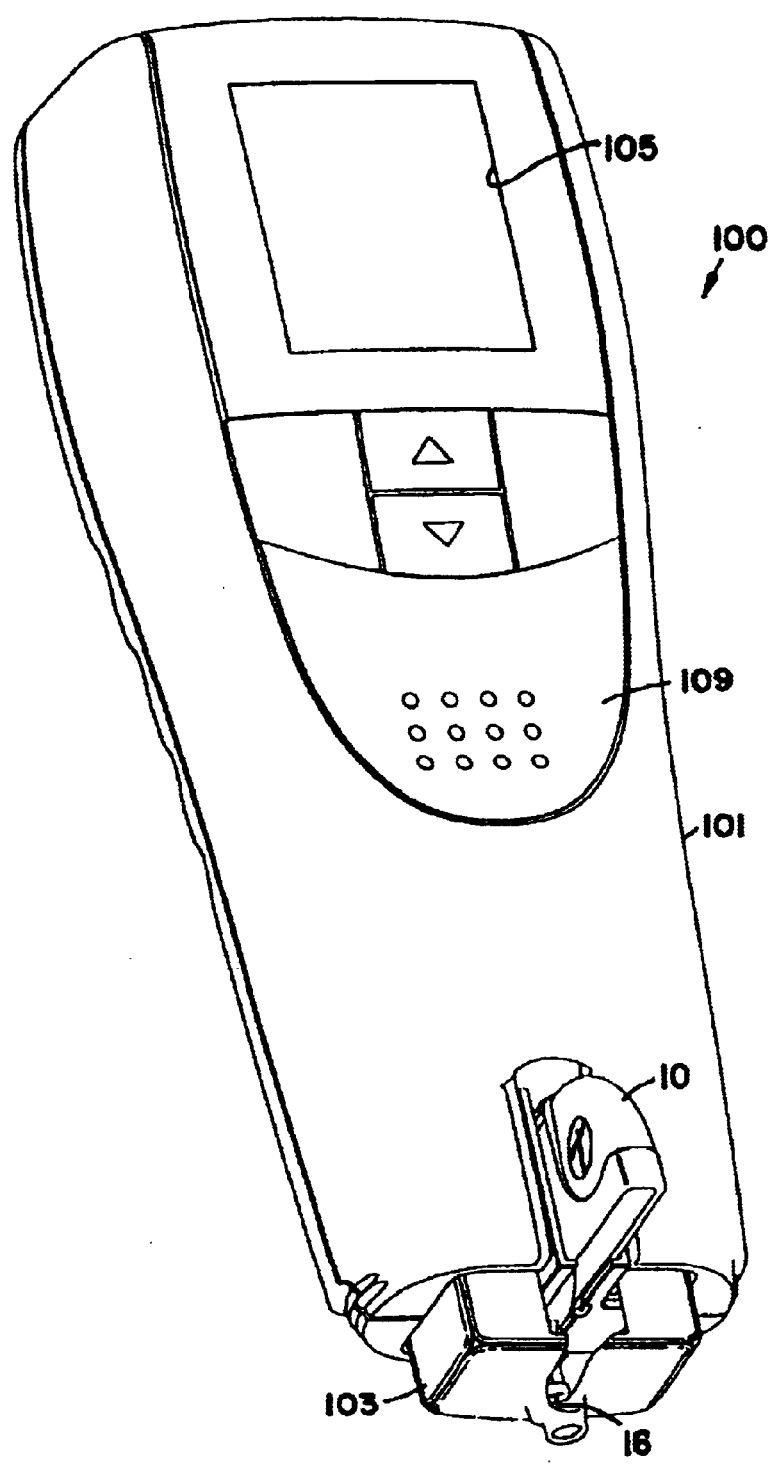
FIG. 1 is a perspective view of a blood glucose test module containing a disposable sampler.

FIG. 1 is an overall view of a test module 100 for testing blood glucose. The test module 100 is a hand-held device and includes a housing 101 containing circuit components as will be described. The test module 100 includes a sampler-receiving end 103 for receiving a disposable sampler 10 having a protruding needle 16. The sampler receiving end 103 also contains IR optic components as will be described. The sampler 10 is movable relative to the housing 101 and is spring biased to project outwardly from the sampler receiving end 103 as more fully described in U.S. Pat. No. 5,682,233 (with reference to FIGS. 28–31 of the '233 patent).

The housing 101 contains a user interface in the form of an LCD display 105 for projecting visual information to a user as will be described. The user interface may also include a buzzer 107 (shown only in FIG. 2) or other audible signal source. The user interface also includes a user input in the form of a keypad 109 to permit a user or technician to input information. For example, the keypad 109 may include a switch to power-up the test module 100.

Figure 2:
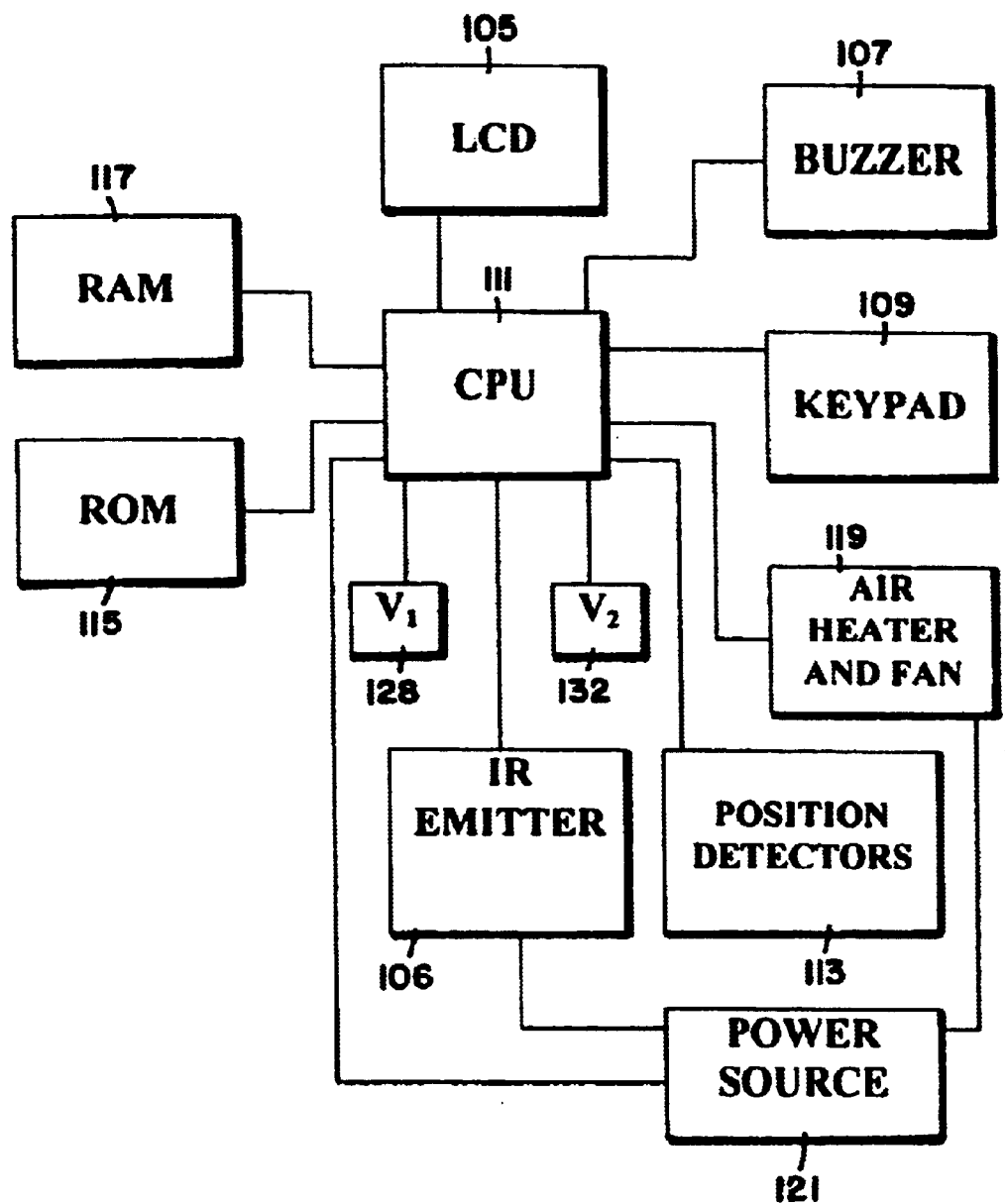
FIG. 2 is a block diagram of components of the test module of FIG. 1.

The test module 100 contains circuit components used in measuring and reporting glucose levels in a sample. These components are schematically illustrated in FIG. 2. The components include a central processing unit (CPU) 111 for controlling operation of the test module 100. Inputs to the CPU 111 include the user keypad 109 as well as position detectors 113. Shown only schematically in FIG. 2, these detectors 113 may include limit switches or other commercially available items to detect the presence of a sampler 10 in the sampler-receiving end 103 or to detect relative positioning of movable components. Also inputted to the CPU 111, are test and reference voltages V1 and V2 from IR detectors 128 and 132 to be more fully described.

A read-only-memory (ROM) 115 and random-access-memory (RAM) 117 are provided connected to the CPU 111. The ROM and RAM memory 115, 117 store operating software and data to effectuate the system logic, which will be described with reference to the flow-chart of FIG. 4. Such data may include stored values of $V_1$ and $V_2$ as well as parameters of empirical formulas (to be described) used in calculating glucose levels based on values of $V_1$ and $V_2$. Such data may also include built in time delays and pulsing times as will be described.

The CPU 111 manipulates stored and collected data according to stored software to control operation of certain output components. For example, the CPU 111 controls pulsing of an IR emitter 106 as well as controlling operation of an air heater and fan 119. The CPU 111 also controls operation of the LCD 105 and the audible signal 107. A power source 121 (e.g., batteries or AC-DC current converter) provides power to all components such as the air heater and fan 119 and provides necessary voltage potentials for operation of circuit components.

Figure 4A:
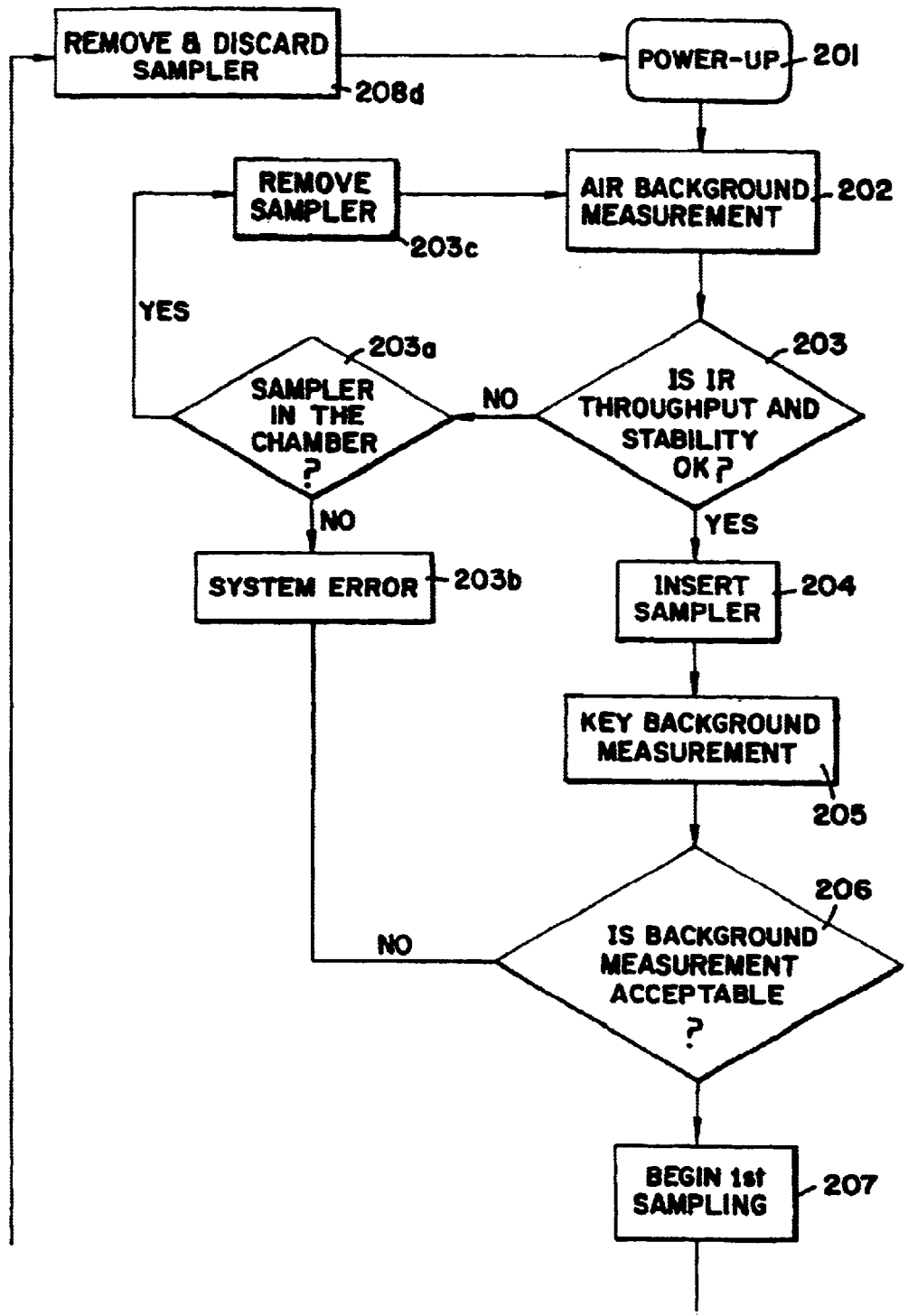
FIGS. 4A, 4B are schematic flow chart of a logic system for a controller for a measuring process using the apparatus of FIG. 1.
Figure 4B:
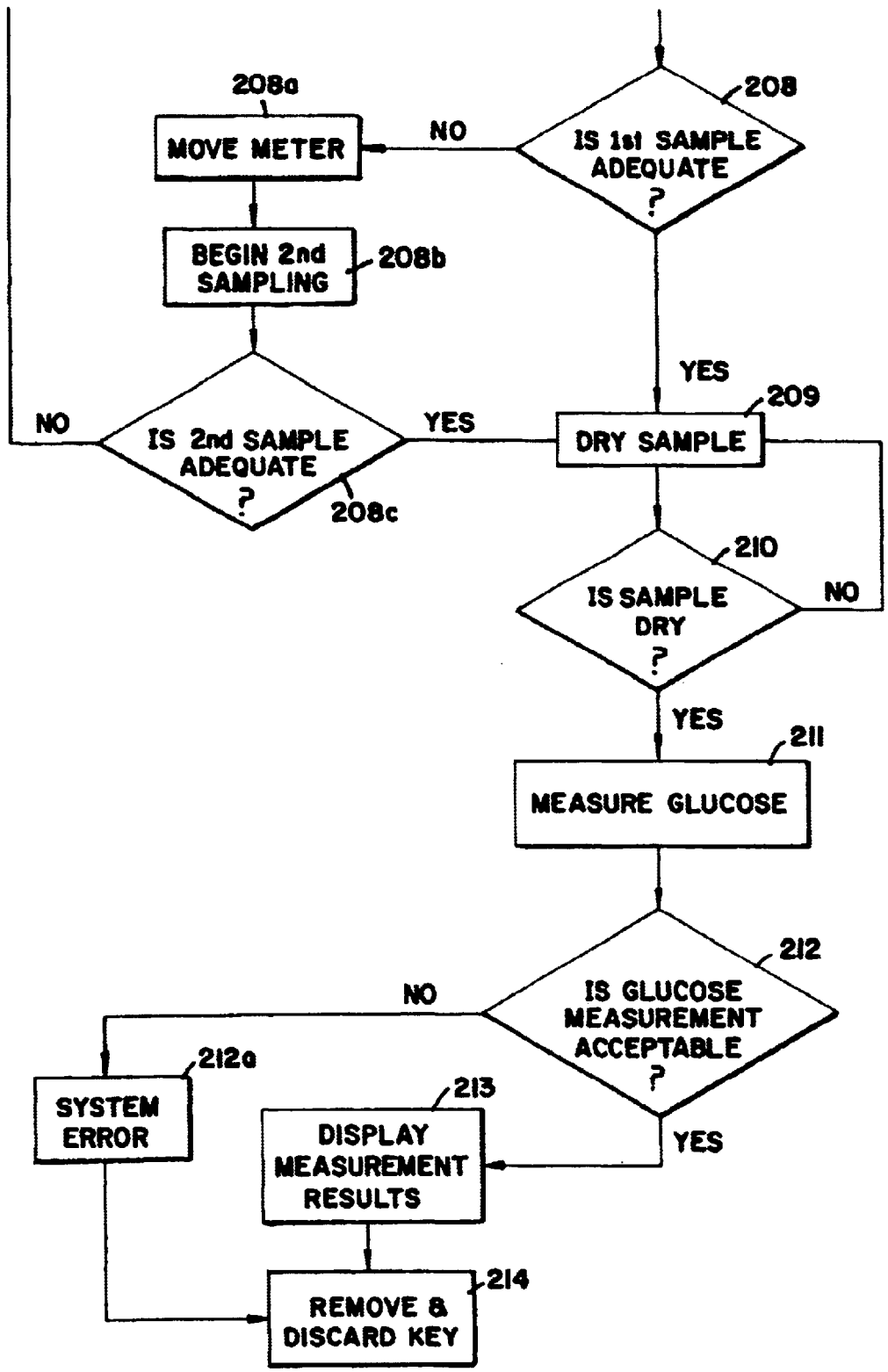

The circuit components and software of the test module 100 are shown schematically in FIG. 2 and 4 and described herein. Details of circuit components and programming code are not described as one of ordinary skill in the art will find such details readily apparent with the benefits of the teachings of the present invention.

Figure 3:
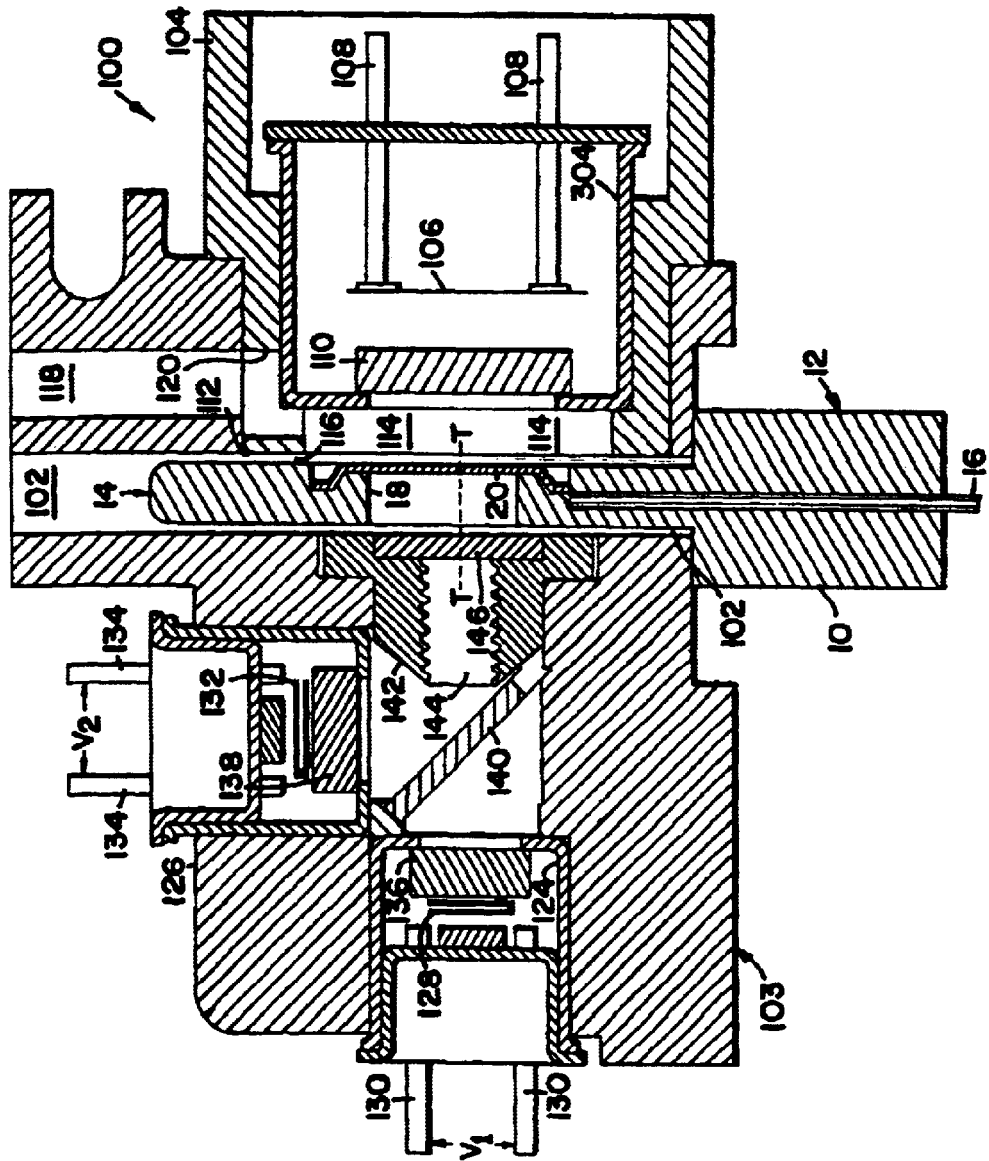
FIG. 3 is a cross-sectional view of a sampler placed within a sampler-receiving end of the test module of FIG. 1 and with a target area of a sampler membrane aligned with optic components of the test module.

With reference now to FIG. 3, a sampler 10 is shown placed within a sampler receiving chamber 102 of the sampler-receiving end 103 of the test module 100. The sampler 10 is such as that shown in U.S. Pat. No. 5,682,233 and identified as sampler 32 in FIG. 18 of that patent. The sampler may also be as that shown as element 410 in U.S. Pat. No. 5,823,973.

The sampler 10 includes a plastic body 12 with a sampling portion 14 sized to be received within chamber 102. The sampler 10 includes a needle 16 which, in a preferred embodiment, is sized to penetrate into but not through a patient's dermis in order to collect a sample of substantially blood-free interstitial fluid in a substantially pain free manner. The sampling portion 14 includes a through-hole 18. An absorbent membrane 20 is placed over the hole 18. The needle 16 is positioned to deposit the collected sample onto the membrane 20 with the deposited fluid evenly distributed over the membrane 20. As more fully disclosed in U.S. Pat. No. 5,823,973, the needle 16 and membrane 20 are mutually positioned for the membrane 20 to act as a filter. The membrane 20 filters out blood cells that might be present in the sample. Such filtering reduces the amount of blood cells that might migrate toward the center test area of the membrane 20. The generally central test area of the membrane 20 is conveniently referred to herein as a target area T.

The test module sampler-receiving end 103 contains an emitter housing. 104 containing an IR emitter subassembly 304, which in turn contains an IR emitter 106 (i.e., a filament) connected by electrical leads 108 to the electrical energy source 121. The power source 121 provides a pulsed signal (e.g., 1.5 Hz) to heat the emitter 106. The heated emitter 106 emits a pulsed broadband IR output including a characteristic or analyte wavelength (e.g., 1040 cm$^{-1}$) that is absorbable by glucose. Being a broadband emitter, the emitter 106 also emits IR wavelengths shorter and longer than the test wavelength for reasons that will become apparent. The emitter 106 is positioned for the emitted wavelengths to be directed toward the target area T. The emitter housing subassembly 304 carries an IR transparent window 110 (e.g., a germanium window) positioned between the emitter 106 and the target area T. The germanium window 110 is transparent to IR in a wide wavelength band surrounding the test wavelength.

The germanium window 110 is spaced inwardly from an axial face 112 of the emitter housing 104 to define a recessed air chamber 114 within the housing 104. The air chamber 114 is axially aligned with the target area T and open facing the membrane 20 at the target area T.

The axial face 112 of the emitter housing 104 is evenly spaced from the sampling portion 14 to define a planar air plenum 116 between the air chamber 114 and the sampling portion 14. The air plenum 116 is radially vented to the atmosphere (i.e., in an airflow direction parallel to the plane of the membrane 20) for the 360° surrounding target area T.

The air heater and fan 119 are carried in the test module main housing 101. A plenum 118 in the test module sampler-receiving end 103 connects an airflow from the heater and fan 119 to an inlet opening 120 in a side of the emitter housing 104. The inlet opening 120 passes heated air into the chamber 114 resulting in the presence of a pressurized volume of heated air in the chamber 114.

Due to the construction so far described, the pressurized air in chamber 114 flows axially toward the membrane 20. Upon impinging on the membrane 20, the heated air spreads out in a radial path flowing 360° around target area T and out through the radial plenum 116. This flow pattern uniformly heats and dries a sample of fluid deposited on the membrane 20 to evaporate and remove water from the sample as will be described.

The test module sampler-receiving end 103 further contains an analyte detector subassembly 124 and a reference detector subassembly 126. The analyte detector subassembly 124 is axially aligned with both the target area T and the IR emitter 106. The axis of the reference housing 126 is 90° offset from the axial alignment.

The analyte detector subassembly 124 contains an IR detector 128 for producing a signal (indicated by test voltage $V_1$) carried on conductors 130 in response to IR energy striking IR detector 128. Similarly, the reference detector subassembly 126 contains an IR detector 132 for producing a signal (indicated by reference voltage $V_2$) carried on conductors 134 in response to IR energy striking IR detector 132. The detector subassemblies 124, 126 are preferably thermally coupled by a thermal conductor (not shown) to equalize the heat of detector subassemblies 124, 126.

An analyte filter 136 separates IR detector 128 from target area T such that an IR radiation impinging on detector 128 must first pass through analyte filter 136. Similarly, a reference filter 138 is provided for IR detector 132 such that an IR radiation impinging on detector 132 must first pass through reference filter 138.

Figure 6:
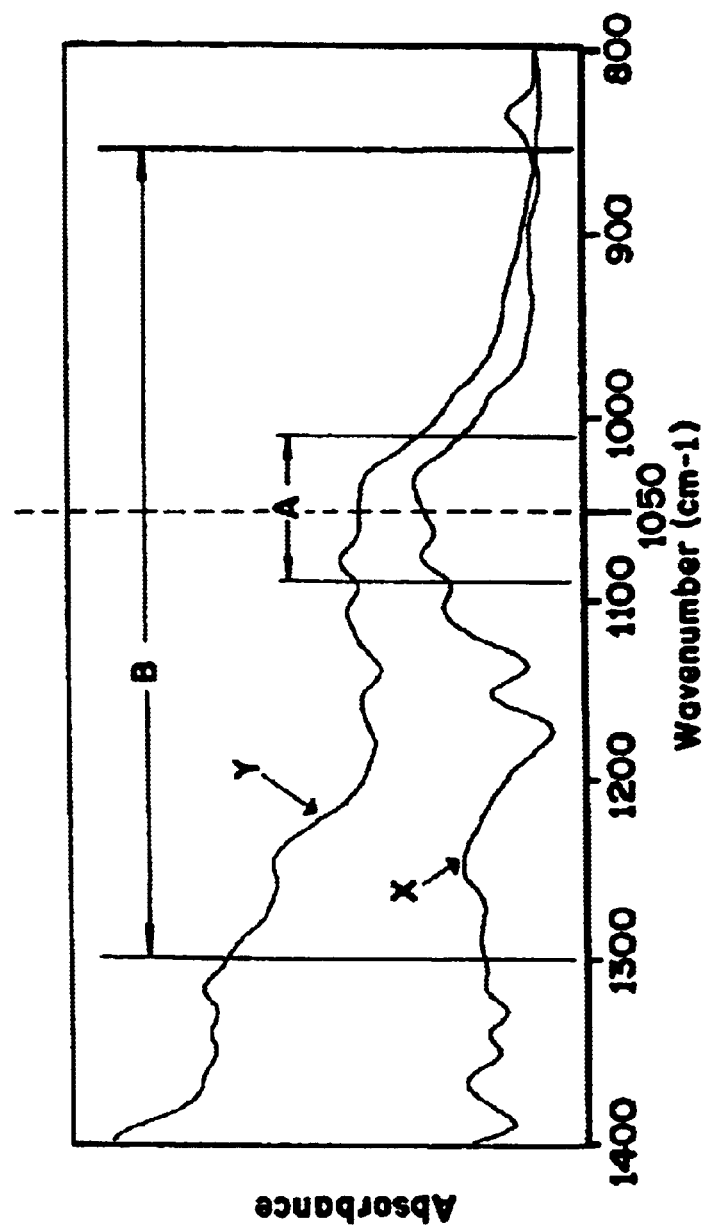
FIG. 6 is a graph comparing IR absorption of glucose over a wavelength band to absorption of other body fluid constituents over the band.

The analyte filter 136 is selected to pass only a narrow IR band A (FIG. 6) centered at about the analyte wavelength (e.g., 1050 cm$^{-1}$ plus or minus 32 cm$^{-1}$). FIG. 6 illustrates the IR absorption of glucose (line X). The glucose IR absorption line X has a plurality of characteristic peaks including a peak at about 1040 cm$^{-1}$ and is low outside of the narrow band A. Other body fluid constituents (e.g., protein) absorb IR energy over a wider band. For example, line Y in FIG. 6, illustrates IR absorption of such constituents over a broad band B. Line Y shows significant absorption at glucose's characteristic wavelength of 1040 cm$^{-1}$ and also shows significant absorption outside of the range of band A. The reference filter 138 is selected to pass a broad IR band B (e.g., 860 cm$^{-1}$ to 1300 cm$^{-1}$).

A beam splitter 140 is contained within the sampler-receiving end 103 between the target area T and analyte filter 136. The splitter 140 is selected to pass a portion of an IR light from target area T to analyte filter 136 and reflect a remainder of the IR light to the reference filter 138. Beam splitters 140 are commercially available to permit a designer to select a wide variety of ratios between a percent of a light signal being passed through the splitter and a percent being reflected. In a preferred embodiment, the beam splitter 140 is selected for the voltages $V_1$ and $V_2$ on conductors 130, 134 (and hence the power output of detectors 128, 132, respectively) to be substantially equal. In a preferred embodiment, splitter 140 will pass 85% of a received IR signal to analyte filter 136 and will reflect the remaining 15% to reference filter 138.

An aperture 142 is mounted between the beam splitter 140 and the target area T. The aperture 142 contains a through-hole 144 to pass IR light from the target area T to the splitter 140. The through-hole 144 may be threaded to scatter reflection off the wall of the aperture 142 to avoid isolated areas of high IR intensity that might otherwise result from reflection. A germanium window 146 seals the aperture 142. The window 146 passes IR radiation from the target area T while sealing the optic components (e.g., filters 136, 138) from contaminants.

With reference now to FIGS. 4 and 5, the invention will be described using the apparatus of FIGS. 1–3 to collect a sample of interstitial fluid and to measure glucose in the collected sample to indicate a patient's blood glucose level.

Initially, a sampler 10 is removed from test module 100 and chamber 102 is empty but for air. As indicated in step 201 of FIG. 4, the test module is turned on by the patient using keypad 109. While not illustrated, the power-up step 201 can be used for the system electronics to self-test the connectivity and operability of system components as is conventional in self-diagnostic electronic circuitry.

After power-up 201 and without a sampler 10 yet inserted into chamber 102, the IR emitter 106 is energized and pulsed (e.g., 40 pulses) during an air background step 202. A resulting IR signal is passed unmodified (but for air absorption of the IR signal) to the beam splitter 140 and subsequently to the analyte and reference detectors 128, 132. Voltages at the analyte and reference detectors 128, 132 are measured during the pulsing. Averages of such measurements are computed over small time intervals. These averages are conveniently referred to as the analyte voltage $V_1$ and reference voltage $V_2$. The voltages $V_1$ and $V_2$ are determined and compared for throughput and stability in step 203. If either of $V_1$ or $V_2$ are below a pre-set minimum, a low throughput is concluded suggesting a contaminant in the apparatus interfering with IR transmission or suggesting that a sampler 10 is within the chamber 102. Stability is determined by calculating a standard deviation of pulses used to calculate $V_1$ and $V_2$. A calculated standard deviation in step 203 greater than a pre-determined maximum suggests instrument mishandling or damage.

In the event the system determines a failure of the throughput and stability test of step 203, the system inquires whether a sampler 10 is in the chamber 102 (step 203a). Such an inquiry can be self-diagnostic (e.g., limit switches 113 detecting presence of a sampler in chamber 102) or an inquiry to a user through a user interface (e.g., a message displayed on a liquid crystal display LCD 105). If no sampler 10 is present in the chamber 102, the system shuts down (step 203a). If a sampler 10 is found, the user is instructed to remove the sampler 10 (step 203c).

In the event the throughput and stability are satisfactorily determined in step 203, a stable average voltage prior to sampler insertion (voltage $V_2^0$) is detected representing a high IR transmission through air. This is graphically illustrated in FIG. 5 as the line segment between times $t_0$ (representing the initiation of power in step 201) and $t_1$ (representing the end of step 203).

Following satisfactory completion of step 203, the user is instructed to insert a sampler 10 into Chamber 112 (step 204). After such insertion, the emitter 106 is pulsed (step 105) and resulting voltages $V_1$ and $V_2$ are again determined and compared for acceptability (step 206). For example, a voltage ratio ($V_1/V_2$) outside of a predetermined acceptable range indicates a system error (e.g., a pre-used sampler) and the system shuts down (step 203b). If an acceptable ratio is determined, the voltages $V_1$ and $V_2$ are stored in memory 117. FIG. 5 illustrates that insertion of a sampler 10 (at time $t_1$) results in a sudden drop in the reference voltage $V_2$ to a new steady-state average voltage $V_{2c}$, which represents a reduced IR transmission due to IR absorption through a clean membrane 20 that contains no sample.

After satisfactory completion of step 206, the user is instructed to initiate sampling (step 207). Sampling is performed by urging the sampler 10 (still in place in the chamber 102) against the skin with the exposed needle 16 penetrating into the dermis. Interstitial fluid within the dermis flows through the needle 16 and is deposited on the membrane 20.

The system determines if sampling is adequate (step 208). This step is best explained with reference to FIG. 5.

As fluid is deposited on the membrane 20, the water-laden fluid spreads over the target area T. The water contained within the fluid absorbs IR. As sampling initiates (corresponding with time $t_2$), the measured reference voltage $V_2$ decreases and continues to decrease as progressively more fluid is deposited on the membrane 20. Sampling is deemed adequate when the measured reference voltage $V_2$ falls below a predetermined level of the average steady-state reference voltage (e.g., 5%$V_{2c}$). Such a reduction in the measured reference voltage $V_2$ indicates an adequate volume of fluid has been collected and dispersed on membrane 20. This step has the advantage of not requiring a pre-set sampling time which merely assumes collection of an adequate amount of sample.

In the event an adequate amount of fluid is not detected in step 208 within a pre-set period of time, the user is instructed to move the test module 100 to try sampling in a different location on the skin (step 208a). The user begins the second sampling effort (step 208b) and the adequacy of the sampling is determined (step 208c) in the same manner as in step 208. If the sampling continues to be unsatisfactory, the user is instructed to replace the sampler 10 and start the process over (step 208d).

The user is advised that sampling is deemed adequate by an audible signal from buzzer 107. This signal advises the user the needle 16 should be moved away from the patient's skin. In the event the sampling is deemed adequate in either of steps 208 or 208c, the system begins to dry the collected sample (at time $t_4$).

The drying process follows a pre-set delay period (e.g., a 10-second delay illustrated as the time between $t_3$ and $t_4$). The delay period ensures the deposited sample flows evenly onto the membrane 20 in the target area T.

The drying step 209 results in the air heater and fan 119 being operated. Warm air flows into chamber 114 and is evenly distributed over the membrane 20. The warm airflow evaporates water from the sample and removes the evaporated water through the air exhaust through plenum 116.

The system determines if the sample is dry (step 210). If not, drying is continued. This determination is explained with reference to FIG. 5. After drying starts (time $t_4$), water is gradually removed from the sample and the IR transmittance through the sample increases. The sample is deemed dry when the measured reference voltage $V_2$ attains a steady-state value exceeding a prescribed floor (e.g., greater than 50% of $V_{2c}$).

With a dry sample, glucose measurement is initiated (step 211). The voltages $V_1$ and $V_2$ are measured and compared. Throughout the glucose measurement, the adequacy of the measurement is assessed (step 212). For example, a steady-state average reference voltage $V_2$ (indicated in FIG. 5 as starting at time $t_5$) as well as a steady-state average analyte voltage $V_1$ are examined. The existence of a steady-state can be determined by the ratio of the measured analyte and reference voltages $V_1$ and $V_2$ having a standard deviation within a prescribed range. If such conditions are not met, an error is determined to exist (step 212a) and the user is instructed to remove and discard the sampler 10 (step 214).

If glucose measurement is deemed acceptable in steps 211 and 212, the system calculates the glucose levels and reports the levels to the user (step 213). The user is then instructed to remove and discard the sampler 10.

The calculation of glucose in step 213 is performed using the measured steady-state average test and reference voltages $V_1$ and $V_2$ from steps 211 and 213 (i.e., the time interval after time $t_5$) and comparing these to average test and reference voltages $V_1$ and $V_2$ measured with a clean sampler 10 (steps 205–206). The measurement of glucose contained within the interstitial fluid sampler indicates the patient's blood glucose level.

Glucose is known to absorb IR at a characteristic wavelength (i.e., 1040 cm$^{-1}$). The analyte filter 136 permits only a narrow IR band (band A in FIG. 6) at this wavelength to pass to detector 128 and be measurable as analyte voltage $V_1$. Therefore, a reduction in the analyte voltage $V_1$ during the glucose measurement step (step 211) from the clean and dry measurement step (step 205) suggests the presence of glucose absorbing IR in the narrow band. However, glucose is not the only possible substance in the sample that can account for the reduction in the analyte voltage $V_1$. Even if no blood cells are present in the sample, proteins and other substances can absorb glucose in the analyte wavelength bandwidth. However, these substances significantly absorb IR radiation over a much broader bandwidth (band B in FIG. 6) than the narrow bandwidth (band A in FIG. 6) passed by test filter 136.

The reference filter 138 passes the broad wavelength band including both those absorbed by both protein and glucose. Absorption due to glucose is considered to be a small percentage of the total absorption. A reduction in the reference voltage $V_2$ during the glucose measurement step (step 211) from the clean and dry measurement step (step 205) indicates the degree of presence of IR absorbing substances other than glucose in the sample. Comparison of the test and reference voltages $V_1$ and $V_2$ before and after sampling in combination with empirical data of test subjects using the apparatus of the present invention and comparing such voltages to glucose measuring using prior techniques (e.g., diluted plasma samples using prior art glucose measurements) permits the development of a formula to calculate glucose. Specifically, regression analysis of such data yields the following formula to calculate glucose:

$$\text{GLUCOSE} = B_0 + B_1(CR) + B_2(PR) + B_3(CR \times PR) \text{ where:}$$

$$CR = ln(V_{1s}/V_{2s})/(V_{1c}/V_{2c});$$

$$PR = ln((K \times V_{2c}) - V_{1s})/((K \times V_{2c}) - V_{1c});$$

and where:

$V_{1s}$ is the test voltage $V_1$ measured during the sample measurement step 211–212;

$V_{2s}$ is the reference voltage $V_2$ measured during the sample measurement step 211–212;

$V_{1c}$ is the test voltage $V_1$ measured during the background step 205–206;

$V_{2c}$ is the reference voltage $V_2$ measured during the background step 205–206; and $B_0$, $B_1$, $B_2$ and $B_3$ are constants resulting from a multi-linear regression analysis comparing the foregoing variables to alternative prior art blood glucose measurements for calibrated samples both with the present invention and such alternative measurements.

The parameter K is a constant determined by a regression analysis comparing PR to known protein levels in calibrated samples. K is a value that minimizes error in the regression. The value of K may vary slightly between different lots of material of membrane 20. Therefore, it is presently anticipated that values of K for a variety of lots will be stored in ROM 115 and a user will input a lot number.

CR represents the proportion of signal within the narrow analyte band that includes glucose and protein. PR represents the proportion of signal outside the narrow analyte band that is due to protein only. The PR ratio is considered to be linearly proportional to the protein signal that lies within the narrow analyte band that is due to protein. Therefore, the effect of protein can be subtracted out and glucose can be determined. The term $B_1$ (CR) represents a total of glucose and protein. The term $B_2$(PR) subtracts out protein from the total. The term $B_3$(CR×PR) adjusts for filter tolerances and spectral (absorbency) variations from instrument to instrument and other possible factors.

The foregoing formula is a mathematics equivalent of using a reference filter that passes only the broadband less the narrow analyte band. Use of such a filter would simplify the calculation of glucose.

The present invention need not calculate or determine the volume of glucose collected because the use of a membrane controls a volume. In the event such volume may be desirable for modifying the tolerance or accuracy of the measurement system, the invention permits a determination representative of the amount of fluid collected. Namely, a small volume of fluid will dry more rapidly than a large volume during the drying steps 209–210. The phantom lines of the curve in FIG. 5 represent the modified shape of the curve in response to a reduced volume of collected fluid. Therefore, relative volume can be determined and used as desired to modify the above-referenced empirical formula.

From the foregoing detailed description, the present invention has been described in a preferred embodiment. Modifications and equivalents of such disclosure are intended to be included in the appended claims.

The claimed invention is:

1. A method for testing for an analyte in a sample having both the analyte and other constituents where the analyte has an absorption peak over a narrow bandwidth at a characteristic wavelength and where the other constituents have an absorption of a broad bandwidth and where the broad bandwidth includes and is broader than the narrow bandwidth, the method comprising:

directing a radiant energy at the sample with a source bandwidth broader than and including the broad bandwidth which includes the narrow bandwidth, wherein a portion of the energy is absorbed by the sample and wherein a remainder of the energy is available for analysis;

analyzing the remainder of the energy by optically filtering the remainder into an analyte portion containing substantially only the narrow bandwidth and a reference portion containing substantially the broad bandwidth and said narrow bandwidth; and measuring and comparing the analyte portion and the reference portion to calculate an amount of the analyte in the sample.

2. A method according to claim 1 wherein said measuring and comparing includes separating out of the reference portion an amount representing absorption in the narrow bandwidth.

3. A method according to claim 1 wherein said separating is mathematically performed.

4. A method according to claim 1 wherein the sample is a water-containing body fluid, the method further comprising removing the water from the sample before directing the radiant energy at the sample.

5. A method according to claim 1 wherein the analyte is glucose, the source bandwidth is infrared radiation and the narrow bandwidth includes a characteristic wavelength of about 1040 cm$^{-1}$.

6. A method for testing for an analyte in a sample having both the analyte and other constituents where the analyte has an absorption peak over a narrow bandwidth at a characteristic wavelength and where the other constituents have an absorption of a broad bandwidth and where the broad bandwidth includes and is broader than the narrow bandwidth, the method comprising:

providing a substrate onto which the sample is to be deposited;

directing a radiant energy at the substrate with a source bandwidth, wherein a portion of the energy is absorbed by the substrate and wherein a first remainder of the energy is available for analysis;

analyzing the first remainder of the energy by filtering the first remainder into a substrate portion containing substantially only the narrow bandwidth and a first reference portion containing substantially only the broad bandwidth;

measuring the substrate portion and the first reference portion;

determining the ratio of the substrate portion to the first reference portion;

depositing the sample onto the substrate;

directing the radiant energy at the sample with the source bandwidth including the broad bandwidth, wherein a portion of the energy is absorbed by the sample and wherein a second remainder of the energy is available for analysis;

analyzing the second remainder of the energy by filtering the second remainder into an analyte portion containing substantially only the narrow bandwidth and a second reference portion containing substantially only the broad bandwidth;

measuring the analyte portion and the second reference portion;

determining the ratio of the analyte portion to the second reference portion; and comparing the substrate portion and the first reference portion to the analyte portion and the second reference portion to calculate the amount of the analyte in the sample.

7. A method according to claim 6 wherein the amount of analyte is calculated according to the following formula:

$$\text{Analyte} = B_0 + B_1(CR) + B_2(PR) + B_3(CR \times PR) \text{ where:}$$

$$CR = ln((V_{1s}/V_{2s})/(V_{1c}/V_{2c}));$$

$$PR = ln((K \times V_{2s}) - V_{1s})/((K \times V_{2c}) - V_{1c});$$

and where:

$V_{1s}$ is an analyte voltage $V_1$ measured during the step of measuring the analyte portion;

$V_{2s}$ is a reference voltage $V_2$ measured during the step of measuring the analyte portion;

$V_{1c}$ is the analyte voltage $V_1$ measured during the step of measuring the substrate portion;

$V_{2c}$ is the reference voltage $V_2$ measured during the step of measuring the substrate portion;

$B_0$, $B_1$, $B_2$ and $B_3$ are constants resulting from a multi-linear regression analysis comparing the foregoing variables to alternative prior blood glucose measurements for calibrated samples;

K is a constant determined by a regression analysis comparing PR to known protein levels in calibrated samples;

CR represents the proportion of signal within the narrow analyte band that includes glucose and protein;

PR represents the proportion of signal outside the narrow bandwidth that is due to protein only;

$B_1(CR)$ represents a total of glucose and protein;

$B_2(PR)$ subtracts out protein from the total; and $B_3(CR \times PR)$ adjusts for filter tolerances and spectral (absorbency) variations.

8. An apparatus for testing for an analyte in a sample having both the analyte and other constituents where the analyte has an absorption peak over a narrow bandwidth at a characteristic wavelength and where the other constituents have an absorption of a broad bandwidth and where the broad bandwidth includes and is broader than the narrow bandwidth, the apparatus comprising:

a chamber for receiving the sample;

a radiant energy source for directing a radiant energy at the chamber with a source bandwidth broader than and including the broad bandwidth which includes the narrow bandwidth;

a filter and energy detection system for analyzing radiant energy from the chamber by filtering the radiant energy from the chamber into an analyte portion containing substantially only the narrow bandwidth and a reference portion containing substantially the broad bandwidth and said narrow bandwidth; and a controller for measuring and comparing the analyte portion and the reference portion to calculate an amount of the analyte in the sample.

9. An apparatus according to claim 8 including a sample collection member for collecting a sample from a patient and depositing the sample in the chamber.

10. An apparatus according to claim 8 including a dryer for evaporating water from a sample in the chamber.

11. An apparatus according to claim 8 wherein the filter and energy detection system includes:
- a beam splitter for splitting the radiant energy from the chamber into an analyte portion and a reference portion;
- a test filter for filtering the analyte portion to pass substantially only the narrow bandwidth;
- a reference filter for filtering the reference portion to pass substantially the broad bandwidth and said narrow bandwidth;
- a analyte detector for producing a signal responsive to an intensity of radiant energy passed by the analyte filter;
- a reference detector for producing a signal responsive to an intensity of radiant energy passed by the reference filter; and
- the analyte and reference detectors connected to the controller to pass the analyte and reference signals to the controller for use in measuring and comparing the signals.

12. A method according to claim 11 comprising testing the sample for the analyte after the measured transmittance attains a stable steady-state value.

13. An apparatus according to claim 8 wherein said source is a source of IR energy.

* * * * *